United States Patent [19]

Engelhard et al.

[11] Patent Number: 5,942,125
[45] Date of Patent: *Aug. 24, 1999

[54] DENTAL UNIT WATER PURIFIER

[75] Inventors: Rolf Engelhard; Stephen P. Kasten, both of Prescott, Ariz.

[73] Assignee: Germiphene Corporation, Ontario, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/648,204

[22] Filed: May 14, 1996

[51] Int. Cl.$^6$ ............................... C02F 1/32; C02F 1/78
[52] U.S. Cl. .................... 210/748; 210/760; 210/764; 210/192; 433/82; 433/88; 433/98; 250/436; 250/437; 422/301; 422/305; 422/186.1
[58] Field of Search .................... 210/760, 192, 210/748, 764; 433/82, 80, 88, 98; 250/436, 432 R, 437; 422/305, 28, 292, 301, 186.06, 186.1

[56] References Cited

U.S. PATENT DOCUMENTS

| D. 357,058 | 4/1995 | Engelhard | D23/209 |
|---|---|---|---|
| 2,970,821 | 2/1961 | Axt | 210/760 |
| 3,336,099 | 8/1967 | Czulak et al. | 210/760 |
| 3,550,782 | 12/1970 | Veloz | 210/192 |
| 3,696,932 | 10/1972 | Rosenberg | 210/437 |
| 3,726,404 | 4/1973 | Troglione | 210/192 |
| 4,021,921 | 5/1977 | Detaille | 32/40 R |
| 4,069,153 | 1/1978 | Gunther | 210/64 |
| 4,141,830 | 2/1979 | Last | 210/192 |
| 4,156,652 | 5/1979 | Wiest | 250/527 |
| 4,176,061 | 11/1979 | Stopka | 210/760 |
| 4,179,616 | 12/1979 | Coviello et al. | 250/527 |
| 4,230,571 | 10/1980 | Dadd | 210/760 |
| 4,273,660 | 6/1981 | Beitzel | 210/760 |
| 4,274,970 | 6/1981 | Beitzel | 210/748 |
| 4,323,810 | 4/1982 | Horstmann | 313/24 |
| 4,422,450 | 12/1983 | Rusteberg | 604/25 |
| 4,437,999 | 3/1984 | Mayne | 210/748 |
| 4,694,179 | 9/1987 | Lew et al. | 250/431 |
| 4,743,199 | 5/1988 | Weber et al. | 433/216 |
| 4,752,401 | 6/1988 | Bodenstein | 210/746 |
| 4,857,204 | 8/1989 | Joklik | 210/695 |
| 4,892,712 | 1/1990 | Robertson et al. | 422/186 |
| 4,913,827 | 4/1990 | Nebel | 210/748 |

(List continued on next page.)

OTHER PUBLICATIONS

"The Dirty Dental Water Dilemma: A Dentist's Opinion", by Robert A. Silver, *Water Conditioning & Purification*, Sep. 1995, pp. 42–47.

"Dental Waterlines: A Source of Contamination", by J. Williams et al., *Infection Control & Sterilization Technology*, Oct. 1995, pp. 14–20.

"Microbial Contamination of Dental Unit Waterlines: Prevalence, Intensity and Microbiological Characteristics", by J. Williams et al., *Journal of the American Dental Association*, vol. 124, Oct. 1993, pp. 59–65.

"Detecting *Legionella Pneumophila* in Water Systems: A Comparison of Various Dental Units", by S.J. Challacombe et al., *Journal of the American Dental Association*, vol. 126, May 1995, pp. 603–608.

"Safe Water in the Dentist's Office", by G. Shaparenko, *Water Conditioning & Purification*, Jun. 1995, pp. 60 and 62–65.

Primary Examiner—Cynthia L. Nessler
Attorney, Agent, or Firm—Cahill, Sutton & Thomas P.L.C.

[57] ABSTRACT

An ozone generator injects and entrains ozone enriched air into water to be used by a dentist or technician during a dental procedure. The ozone entrained in the water will eliminate the motility and viability of any microbes and pathogens present in the water or in biofilm present in the water lines or channels conveying water to a patient's oral cavity. The ozone generator may be used in combination with water from a municipal water source or from bottled water. Alternatively, the ozone generator may be incorporated within a bottle supplying distilled or otherwise puritied water.

17 Claims, 2 Drawing Sheets

U.S. PATENT DOCUMENTS

| | | | |
|---|---|---|---|
| 4,968,437 | 11/1990 | Noll et al. | 210/748 |
| 5,029,252 | 7/1991 | Ameseder | 422/24 |
| 5,082,558 | 1/1992 | Burris | 210/167 |
| 5,106,495 | 4/1992 | Hughes | 210/139 |
| 5,106,501 | 4/1992 | Yang et al. | 210/266 |
| 5,120,219 | 6/1992 | De Farey | 433/88 |
| 5,120,450 | 6/1992 | Stanley, Jr. | 210/748 |
| 5,120,512 | 6/1992 | Masuda | 422/297 |
| 5,141,636 | 8/1992 | Flanagan et al. | 210/209 |
| 5,158,454 | 10/1992 | Viebahn | 433/88 |
| 5,178,755 | 1/1993 | LaCrosse | 210/195.1 |
| 5,178,758 | 1/1993 | Hwang | 210/256 |
| 5,180,499 | 1/1993 | Hinson et al. | 210/706 |
| 5,207,993 | 5/1993 | Burris | 422/256 |
| 5,213,773 | 5/1993 | Burris | 422/256 |
| 5,266,215 | 11/1993 | Engelhard | 210/748 |
| 5,268,104 | 12/1993 | Massoomain | 210/638 |
| 5,302,298 | 4/1994 | Leitzke | 210/768 |
| 5,393,490 | 2/1995 | Jacob | 422/22 |
| 5,431,861 | 7/1995 | Nagahiro et al. | 261/140.1 |
| 5,520,893 | 5/1996 | Kasting, Jr. et al. | 422/305 |
| 5,540,848 | 7/1996 | Engelhard | 210/760 |
| 5,547,590 | 8/1996 | Szabo | 210/748 |
| 5,709,799 | 1/1998 | Engelhard | 210/748 |

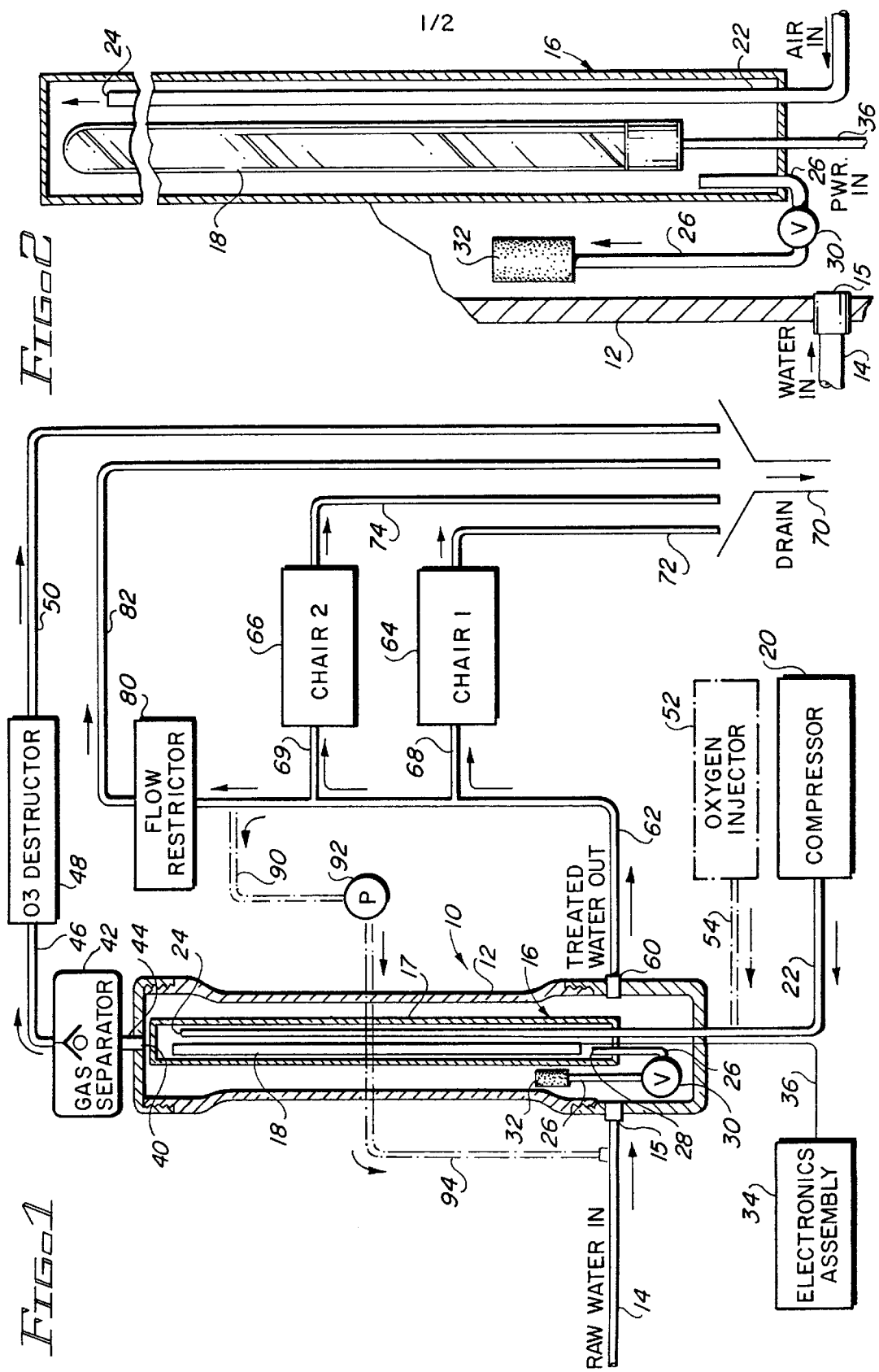

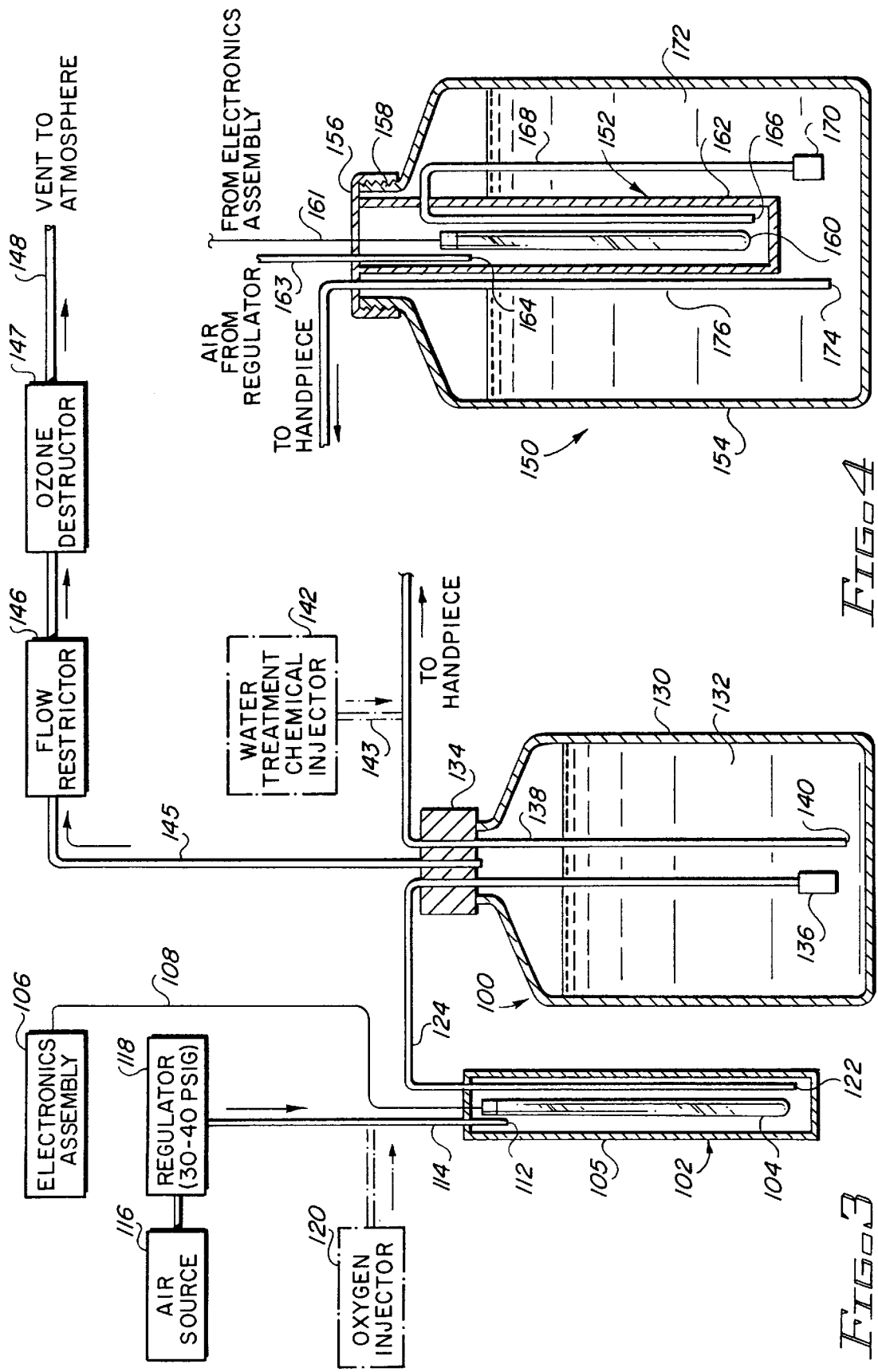

DENTAL UNIT WATER PURIFIER

BACKGROUND OF THE INVENTION

1. Field of the Invention

The present invention relates to purification of dental water lines and, more particularly, to ozonating dental water lines in order to provide uncontaminated water at the point of use.

2. Description of Related Art

Tap water in dental offices is similar to tap water in most homes and offices. While this water is generally considered safe to drink, it is never sterile. Most tap water samples contain fewer than 50 cfu of bacteria per milliliter (cfu/ml). However, once the water leaves plumbing lines and enters the long plastic tubing that feeds into dental high-speed handpieces and other dental implements, such as air-water syringes and ultrasonic tooth scalers, the environment changes. Here, the low flow rate, frequent periods of stagnation and large relative surface area of the small bore plastic lines are ideal for microbial contamination.

Water that stagnates in plastic water lines and/or tubing overnight and even during long periods during the day provide bacteria the opportunity to stick to the wall of the lines/tubing. Water, slowly running through the line, provides a constant flow of bacteria that can adhere to the microbes that are already clinging to the wall. A cooperating population of several different species, which depend on each other for survival, continue to multiply and form a matrix that provides nutrients and mutual protection.

This bacterial population is known as biofilm, a microbial mass that is bathed in liquids. Dental plaque is another example of biofilm. Biofilm can also be found in air conditioning units, artificial implants and many types of equipment, including dental anti-siphon and check valves.

The function of the anti-siphon and check valves is to prevent aspiration of patients' fluids into the dental water lines. Unfortunately, these valves often fail to work properly because of biofilm and other factors.

Microbes can get sucked back into the dental water lines as a result of imperfect hygiene or sterilization practices, a transient negative pressure when the drill stops rotating and/or mechanical failure of anti-siphon valves or other mechanisms. Once this happens, pathogens originating from patients' mouths can enter the lines and adhere to existing biofilm and multiply within them.

These microbes, originating both upstream from municipal water supplies and downstream from patients' blood and saliva, are not very numerous initially. Amplification of the microorganisms is nothing less than astounding. Microbial studies of dental water lines reveal bacterial population explosions averaging over 500,000 cfu/ml and often exceeding 1,000,000 cfu/ml.

Thus far, researchers have identified pathogens and opportunists in dental equipment such as Pseudomonas, Legionella, Staphylococci, Streptococci, Nocardia, Serratia, Klebsiella, Moraxella, Bacteroides, Flavobacterium, Escherichia, several species of amoebae known to serve as hosts for *Legionella pneumophila* and even nematodes (worms).

Various solutions to prevent exposure of dental patients to contaminated water have been proposed. Such proposals include flushing the dental water lines with distilled water or chemicals but little evidence exists that such flushing eliminates the biofilm. Sterilization of dental instruments between patients has little effect in preventing the microbes in the dental water from entering the next patient's mouth. Using new disposable sterile water lines between patients does not solve the problem of biofilm upstream of the replaced lines and the costs are significant. Use of containers having sterile or distilled water is effective only if the water conveying lines are replaced after each patient arid if the water does not become contaminated prior to disposal of used water lines. Use of check valves to prevent backflow is essentially ineffective one hundred percent of the time due to contamination of the valve itself. Use of electrical current in combination with antimicrobial agents is impractical due to unavailability of inexpensive ready-to-use equipment. Distilling the water received from a municipal water source only addresses the water and not the contaminants present in the lines conveying the water to the patient. To date, devices using 0.2 micron filters or the like is reasonably effective to prevent transmission therepast of microbes provided that the filters are replaced at least daily and that the process of such replacement does not permit a colony of microbes to be conveyed to a water line downstream of the filter. It is therefore evident that a significant health hazard exists for patients within a dental office and no viable solution is presently commercially available.

SUMMARY OF THE INVENTION

In the present invention, an ozone generator provides an outflow of ozone enriched air that is introduced to a water source through a sparger or the like to entrain the ozone enriched air in the water. The ozonated water is conveyed through water lines to each of the various handpieces or water flow dependent implements used by a dentist during the normal course of providing dental services. The ozone introduced into the water will destroy any microbial pathogens in the water and render it essentially microbe free. Furthermore, the living organisms in any biofilm attendant the walls of the water lines will be destroyed upon contact with the ozone. Thus, the water delivered to a patient's oral cavity during the rendering of dental services will be essentially free of any viable microbial activity.

It is therefore a primary object of the present invention to provide apparatus for delivering water from dental water lines free of any living microbes.

Another object of the present invention is to provide apparatus for destroying any biofilms formed on the walls of water lines.

Yet another object of the present invention is to provide apparatus that delivers to a dental patient water free of microbial activity whether such water be from a municipal water system or a water container.

Still another object of the present invention is to provide apparatus for destroying any microbes present in a dental water line or the water itself each time water flows through the line.

A further object of the present invention is to provide ozonated water to dental handpieces and other dental implements.

A yet further object of the present invention is to provide inexpensive apparatus for ensuring that water delivered to a dental patient is free of living microbes.

A still further object of the present invention is to provide a method for inexpensively and effectively treating and purifying water delivered to dental handpieces.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates apparatus for ozonating water delivered to a dental chair;

FIG. 2 illustrates details of the ozonating apparatus shown in FIG. 1;

FIG. 3 illustrates apparatus for ozonating water within and delivered from a water container to a dental chair; and FIG. 4 illustrates apparatus contained within a water container for delivering ozonated water from the container to a dental chair.

DETAILED DESCRIPTION OF THE PREFERRED EMBODIMENT

Ozone entrained in water will destroy microbial life forms in the water itself as well as in any biofilm on the containers for the water or upon the walls of channels or lines through which the ozonated water flows because ozone is a viricide, bactericide, and algicide. Referring to FIG. 1, there is shown apparatus 10 for ozonating water entering a dental office to provide ozonated water to each dental chair. The ozonated water will destroy any microbes or pathogens within the water and reduce or terminate the motility and viability of microbial activity in any biofilm that may be present on the walls of the water lines and attendant dental implements. Furthermore, the ozonated water will terminate the motility and viability of any microbes or pathogens aspirated from a patient and entering any water channels in the dental implements and the water lines extending from the dental implements.

With joint reference to FIGS. 1 and 2, apparatus 10 includes a container 12 for receiving water from a water line 14. An ozone generator 16 is disposed within container 12 and includes a lamp or tube 18 for emitting ultraviolet light within a watertight steel cylinder 17. A compressor 20 provides a source of air under pressure through pipe 22 into ozone generator 16. Outlet 24 of pipe 22 may be at the upper end of the ozone generator, as illustrated. A pipe 26 extends from within the ozone generator and includes an inlet 28 located at the lower end of ozone generator 16. Thereby, air flowing into the generator through outlet 24 is forced to pass around and along tube 18 to inlet 28 to increase the exposure of the air to the ultraviolet radiation from the tube. It is well known that the oxygen in the air subjected to ultraviolet light will result in conversion of the oxygen molecules into ozone molecules as a function of the intensity of and exposure time to ultraviolet radiation. Thus, ozone enriched air flows into pipe 26 through inlet 28. A check valve 30 in pipe 26 prevents reverse flow therethrough. Pipe 26 is terminated by a sparger 32. The sparger emits the ozone enriched air in the form of tiny bubbles which become readily entrained in the water in and flowing through container 12.

An electronics assembly 34, connected to a suitable power source, provides the requisite electrical power through conductor 36 to tube 18 to bring about energization of the tube and emission of ultraviolet radiation. To prevent an accumulation of ozone enriched air within container 12, any such gaseous compound is evacuated through an outlet 40 leading to a gas separator 42 through a pipe 44. Outflow from the gas separator is through a pipe 46 to an ozone destructor 48. The remaining air is discharged through a pipe 50 to a drain or the like to accommodate drainage of any moisture that may accumulate downstream of container 12.

As an alternative to air injection, oxygen may be injected into ozone generator 16 to provide a higher concentration of ozone in the gas discharged from sparger 32. A source of oxygen and an injector for propelling oxygen into the ozone generator is represented by numeral 52 identifying an oxygen injector. The oxygen is injected through pipe 54 into the ozone generator. It is to be understood that injection of air or oxygen is primarily in the alternative although oxygen enriched air could also be injected.

The ozonated water produced within container 12 is discharged through outlet 60 into conduit 62. The conduit serves as a water line to provide ozonated water at each of chairs 64,66, etc. in a dental office. In particular, branch lines 68,69 may extend from conduit 62 to a manifold or the like attendant each dental chair and in fluid communication with dental implements and other devices that normally discharge the water received. Waste water generated at chair 64 is conveyed to a drain 70 through drain line 72. Similarly, waste water generated at chair 66 is conveyed to the drain through drain line 74. Such drain lines would be present for each chair.

Ozone entrained in water is somewhat unstable and will revert to the molecular form of oxygen at a higher or lower rate depending upon a number of variables. To ensure a fresh supply of ozonated water within conduit 62 after periods of inactivity or non-flow of ozonated water through one or more of branches 68,69, a flow restrictor 80 may be employed. Such flow restrictor accommodates a low flow rate of ozonated water continuously through conduit 62 into discharge pipe 82 and drain 70. Alternatively, a return line 90 is in fluid communication with conduit 62 downstream of the last branch leading to a dental chair. Ozonated water from conduit 62 is drawn into the return line by a pump 92. The pump conveys the ozonated water through return line 94 into water line 14 upstream of inlet 15 in container 12. Thus, the ozonated water flowing through the return lines, which water may have a lowered concentration of entrained ozone, is reintroduced to the ozone generator. Such reintroduction, rather than simply having the ozonated water recirculate through conduit 62 and the return line, ensures that water having at least a minimal level of entrained ozone is always present at each of the branch lines (such as branch lines 68,69).

For reasons set forth above, a number of dental offices have begun to use bottles of distilled or purified water instead of relying upon the municipal water system to satisfy the water needs. Referring to FIG. 3, there is illustrated a variant apparatus 100 for use in conjunction with such bottled water. An ozone generator 102 includes a lamp or tube 104 disposed within a closed steel cylinder 105 and connected to an electronics assembly 106 through a conductor 108. Upon energizing the electronics assembly, electrical power is provided to tube 104 causing it to emit ultraviolet radiation. The air within cylinder 105 of the ozone generator will be irradiated to cause a molecular change of the oxygen into ozone. An inflow of air is provided from outlet 112 of pipe 114 connected to an air source 116 under pressure. A regulator 118 may be disposed in pipe 114 to regulate the pressure of the air flowing into the ozone generator. As suggested by the dashed box identified as an oxygen injector 120, oxygen may be discharged through outlet 112 into the cylinder or a mixture of air and oxygen may be discharged into the cylinder. The ozone enriched air within cylinder 105 flows out through inlet 122 up pipe 124. As illustrated, outlet 112 and inlet 122 are at opposite ends of tube 104 to maximize exposure of the air to the ultraviolet radiation emitted from tube 104 and thereby enhance the ozone enriched air.

Bottle 130 containing distilled or otherwise purified water 132 includes a stopper 134 for sealing the bottle against contact between the ambient air and water 132. Pipe 124 extends through stopper 134, as illustrated, and is terminated by a sparger 136 located in proximity to the bottom of bottle 130. The purpose of the sparger is that of discharging the ozone enriched air into the water in the form of tiny bubbles to enhance entrainment within the water. A discharge conduit 138 includes an inlet 140 proximate the bottom of bottle 130. The ozone enriched water (ozonated water) within bottle 130 is conveyed via discharge conduit 138 through stopper 134 to the various dental handpieces or other water related dental implements. Thereby, these handpieces and implements are supplied with ozonated water which will have the effect of destroying the motility and killing any bacteria or other microbes present in either the water or in any biofilm on the wall of the discharge conduit or the walls of channels in the handpieces or dental implements. Under certain circumstances, it may be beneficial to treat chemically the water flowing to the dental handpieces and other implements. This may be accomplished by incorporating a chemical injector 142 in fluid communication via conduit 143 with discharge conduit 138 downstream of bottle 130.

A certain amount of ozone enriched air will separate from water 132 and collect at the top of bottle 130. This ozone is discharged through line 145 extending through stopper 134 from within the bottle. The impetus for such discharge results from the pressure within the bottle generated by the inflowing ozone enriched air through sparger 136. The rate of ozone discharge through line 145 is controlled by flow restrictor 146. To prevent damage to the ambient environment, an ozone destructor 147 eliminates the ozone molecules such that the resulting venting through outlet 148 is a gas essentially ozone free.

Referring to FIG. 4, there is illustrated a further variant apparatus 150 similar to variant apparatus 100 shown in FIG. 3 except that ozone generator 152 is disposed within bottle 154. The ozone generator may be suspended from or otherwise attached to a cap 156 in threaded engagement with neck 158 of bottle 154. A lamp or tube 160 for emitting ultraviolet radiation is disposed within a closed steel cylinder 162 of ozone generator 152. It is electrically connected to an electronics assembly via a conductor 161. Air, oxygen, or a mixture of air and oxygen is pumped into the ozone generator through a pipe 163 having an outlet 164 proximate one end of tube 160. The ozone enriched air produced by radiation from tube 160 is discharged into inlet 166 of pipe 168. The pipe, which may extend through a wall of cylinder 162, as illustrated, discharges the ozone enriched air through a sparger 170 located in proximity to the bottom of bottle 154 to enhance entrainment of the ozone enriched air in water 172 as the minute bubbles from the sparger migrate upwardly. The ozone enriched water or ozonated water is discharged from within bottle 154 through inlet 174 of conduit 176. As indicated, conduit 176 conveys the ozonated water to the dental handpieces and other dental implements using water as part of their function. As noted in the drawing, the air flow from outlet 164 to inlet 166 within cylinder 162 is essentially along the full length of tube 160 to enhance exposure of the air to ultraviolet radiation and thereby promote transformation of the oxygen molecules into ozone molecules.

It is to be understood that a gas other than air can be injected into the ozone generator provided that such gas contains oxygen molecules that can be transformed to ozone upon application of ultraviolet radiation.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. A method for destroying microbes within water lines conveying water from a container to dental handpieces and within any of the channels of the dental handpieces conveying water by subjecting the microbes to the presence of ozone, said method comprising the steps of:

(a) providing a source of oxygen containing gas under pressure in the range of about 30 psig to about 40 psig;

(b) generating ozone from the gas under pressure within a UV opaque member to produce ozone enriched gas, said step of generating being performed within the container;

(c) conveying the ozone enriched gas into the water within the container to be directed to the dental handpieces and to pressurize the water at a pressure above ambient pressure;

(d) entraining the ozone enriched gas in the water to produce ozone enriched water; and (e) further conveying the ozone enriched water through the water lines to the handpieces and through channels of the handpieces to destroy any microbes that come in contact with the ozone in the ozonated water.

2. The method as set forth in claim 1 including the step of recirculating unused ozonated water from the water lines to the water to be entrained with ozone to increase the ozone concentration in the ozonated water.

3. The method as set forth in claim 1 wherein said steps of conveying and entraining are performed within the container.

4. The method as set forth in claim 1 wherein said step of generating comprises the step of urging flow of the oxygen containing gas past a source of ultraviolet radiation.

5. The method as set forth in claim 3 wherein the container includes a cap for sealing the container and including the step of supporting the ozone generator from the cap.

6. Aparatus for entraining ozone in a fluid to be delivered to a water manifold and associated conduits in fluid communication with dental implements to destroy microorganisms that may be present in the fluid, on the surfaces of the conduits and on the surfaces of the dental implements, said apparatus comprising in combination:

(a) an ozone generator for generating ozone comprising a source of UV radiation, a member for housing said UV radiation source, said member being opaque to UV radiation and able to withstand at least twice atmospheric pressure;

(b) a source in fluid communication with said member for conveying an oxygen containing gas under pressure of at least two atmospheres into said member to accommodate ozone generation under pressure in said ozone generator;

(c) a pressurizable container of fluid to be ozonated to provide a source of ozonated fluid to the manifold, the conduits and the dental implements, said ozone generator being disposed within said container;

(d) a device disposed in said container and in fluid communication with said ozone generator for entraining the ozone under pressure in the fluid within said container to enhance the level of ozone concentration in the fluid and to produce an ozonated fluid; and (e) an outlet of said container in fluid communication with the manifold, the conduits and the dental implements to interconnect said outlet with the manifold, the conduits and the dental implements to convey the ozonated fluid to the manifold, the conduits and the dental implements.

7. The apparatus as set forth in claim 6 including a return line in fluid communication with said outlet and said container for returning all or part of the ozonated fluid downstream of said outlet to said container.

8. The apparatus as set forth in claim 6 including a vent in fluid communication with said container for venting gas from said container.

9. The apparatus as set forth in claim 6 including an inlet in fluid communication with said container for conveying fluid to said container.

10. The apparatus as set forth in claim 9 including a return line in fluid communication with said outlet and said inlet for returning all or part of the ozonated fluid downstream of said outlet to said inlet.

11. The apparatus as set forth in claim 6 wherein said ozone generator includes a steel cylinder.

12. The apparatus as set forth in claim 6 wherein the pressure within said member is from about 30 psig to about 40 psig.

13. The apparatus as set forth in claim 6 wherein said entraining device is a sparger.

14. Apparatus for treating water to destroy microbes present in a source of water supplying water to a manifold attendant a dental chair in a dental office, which manifold is in fluid communication with dental implements that normally discharge water as part of their operation and to destroy microbes present in the dental implements and in biofilm attendant conduits extending upstream from the dental implements by ozonating the water to subject the microbes to ozone upon flow of the ozonated water therepast, said apparatus comprising in combination:

(a) an ozone generator, said ozone generator including:
  (i) a UV opaque member capable of withstanding an internal pressure of at least two (2) atmospheres;
  (ii) a source of UV radiation disposed within said member for transforming at least some oxygen molecules contained in a gas within said member into ozone to produce an ozone enriched gas;

(b) a source for the oxygen containing gas under greater than ambient pressure in fluid communication with said ozone generator, said gas source being adapted to convey the gas under pressure to said ozone generator and to maintain the gas within said member at a pressure above ambient pressure;

(c) a container in fluid communication with the source of water and adapted to receive and maintain the water under a pressure greater than ambient pressure for delivery of the water to the manifold, said container including:
  (i) said ozone generator located therein within; and
  (ii) a sparger in fluid communication with said ozone generator for entraining the ozone containing gas from within said ozone generator into the water within said container to produce the ozonated water;

(d) a further conduit in fluid communication with said container and the manifold for discharging the ozonated water from said container to said manifold to subject and kill any microbes present in the manifold, the dental implements and the conduits upstream of the dental implements;

(e) a gas separator in fluid communication with said container for removing from said container any gas not entrained in the water within said container, said gas separator being adapted to maintain a pressure within said container at an above ambient pressure;

(f) means for draining water on command from said further conduit; and (g) means for destroying the ozone present in any gas removed by said gas separator.

15. The apparatus set forth in claim 14 including means for returning ozonated water from said further conduit to said container.

16. The apparatus set forth in claim 14 wherein said source of gas includes a compressor for creating an above ambient pressure within said member.

17. The apparatus set forth in claim 16 wherein the pressure within said member is in the range of about 30 PSIG to about 40 PSIG.

* * * * *